(12) United States Patent
Giacomini et al.

(10) Patent No.: US 12,023,450 B2
(45) Date of Patent: Jul. 2, 2024

(54) STIMULATION DEVICE AND METHOD OF USE

(71) Applicants: Jean Philippe Giacomini, Lexington, KY (US); Thomas Pownall, Lima, NY (US)

(72) Inventors: Jean Philippe Giacomini, Lexington, KY (US); Thomas Pownall, Lima, NY (US)

(*) Notice: Subject to any disclaimer, the term of this patent is extended or adjusted under 35 U.S.C. 154(b) by 0 days.

(21) Appl. No.: 17/050,257

(22) PCT Filed: Apr. 25, 2019

(86) PCT No.: PCT/US2019/029212
§ 371 (c)(1),
(2) Date: Oct. 23, 2020

(87) PCT Pub. No.: WO2020/023093
PCT Pub. Date: Jan. 30, 2020

(65) Prior Publication Data
US 2021/0060287 A1 Mar. 4, 2021

Related U.S. Application Data

(60) Provisional application No. 62/662,618, filed on Apr. 25, 2018.

(51) Int. Cl.
*A61M 21/00* (2006.01)
(52) U.S. Cl.
CPC ..... *A61M 21/00* (2013.01); *A61M 2021/0022* (2013.01); *A61M 2021/0055* (2013.01); *A61M 2205/33* (2013.01)

(58) Field of Classification Search
CPC ....... A61M 21/00–02; A61H 19/00–50; A61H 21/00; A61H 23/00–06; A61H 15/00–02; A61H 37/00; A61H 39/007; A61H 2201/12–149; A61H 2201/50–5097
See application file for complete search history.

(56) References Cited

U.S. PATENT DOCUMENTS

| | | | |
|---|---|---|---|
| 6,193,678 B1* | 2/2001 | Brannon | A61H 23/0263 601/15 |
| 2010/0049177 A1 | 2/2010 | Boone, III et al. | |
| 2010/0318007 A1* | 12/2010 | O'Brien | A61M 21/02 601/48 |
| 2012/0046579 A1* | 2/2012 | Radl | A61H 11/00 601/46 |
| 2013/0018289 A1* | 1/2013 | Nussbaum | A41D 19/0027 601/46 |
| 2013/0158452 A1* | 6/2013 | Juto | A61H 23/04 601/46 |
| 2016/0030281 A1* | 2/2016 | Shafieloo | A61H 23/0245 601/48 |
| 2017/0112716 A1* | 4/2017 | Rawls-Meehan | A61G 7/015 |

(Continued)

*Primary Examiner* — Thaddeus B Cox
(74) *Attorney, Agent, or Firm* — BakerHostetler (57) ABSTRACT

The disclosure provides for a device and method for vibrational, electrical, and magnetic therapy. The device may include a main controller board, a power source, a power switch harness connected to the power source, a vibration module comprising two to more motors capable of generating a multidirectional mechanical vibration, and an input controller. The device may further produce a micro-electrical current and a micro-magnetic field.

21 Claims, 5 Drawing Sheets (56) References Cited

U.S. PATENT DOCUMENTS

| | | | |
|---|---|---|---|
| 2017/0182517 A9 | 6/2017 | Houston et al. | |
| 2017/0290736 A1* | 10/2017 | Idris | A41D 1/005 |
| 2018/0228689 A1* | 8/2018 | Lach | A61H 9/0078 |
| 2018/0356890 A1* | 12/2018 | Zhang | A61B 5/1104 |
| 2019/0110949 A1* | 4/2019 | Bhatti | A61H 23/02 |
| 2019/0298605 A1* | 10/2019 | Rabolt | A61H 23/0263 |

* cited by examiner

STIMULATION DEVICE AND METHOD OF USE

CROSS REFERENCE TO RELATED APPLICATIONS

This application claims priority to U.S. Provisional Application No. 62/662,618, filed Apr. 25, 2018, the contents of which are entirely incorporated by reference herein.

FIELD

The present disclosure is directed to a device for mechanically, electrically, and magnetically stimulating a human or animal and methods of use.

BACKGROUND

The training of humans and animals requires focus and a state of alert relaxation. Both humans and animals are sensitive to the heartbeat, pulse rate, body language, and vocal tone of their trainers.

When subjected to a repetitive, painless tactile stimulus, the body/muscle/nervous system may acquire a new memory and may be used by a trainer to impart relaxation and improve retention of learned behavior. Manual "endotapping" involves rhythmically inconsistent manual stimulation techniques, such as the use of fingertips, hands, or a padded wand to produce tapping. This manual tapping is a "perceptual" (influenced by immediate feedback from the human/animal being tapped) form of vibration that can be applied at a range of frequencies (for example, timed with a movement/gait to influence/modify/ optimize its form and range, rapid to induce relaxation, alternating between slow and rapid to help establish "alert relaxation" or "relaxed movement"). The sequence of response to this repetitive, painless stimulus is always consistent: the person/animal touched first "resist"the stimulus (by fidgeting away or pushing against the stimulus, known as the "opposition reflex"), "ignores" the stimulus (desensitization period), "relax" (giving signs of endorphin/dopamine/oxytocin releases), "learn" (improves the behavior or increase the motion range) and "retain" (the new behavior/movement becomes habitual after a varying number of repetitions). However, this manual tapping requires a human operator to be present and ready, who may be inefficient (too strong or too weak) or untimely (too early, too late), or too slow (not capable to deliver a quick enough stimulus—under 10 Hz). The operator can also be emotionally involved and alter the outcome negatively.

Accordingly, though the Endotapping method has been effective at creating new behaviors or improve biomechanics by accessing the relax phase and the cognitive phase of the trainee, there remains a need to improve the efficiency of Endotapping and improve the appropriateness, timeliness and duration of its delivery without the intervention of a human operator (who may not be available or prepared to operate at the moment of need (typically a stressful moment), in particular to provide adequate repetitions to establish and improve the retention phase. These and other needs are provided in this disclosure.

BRIEF SUMMARY

The disclosure provides for a therapy device, comprising: a main controller board enclosed in a housing; a power source operatively connected to the main controller board; at least one vibration module operatively connected to the main controller board, the vibration module comprising two or more motors, the vibration module operable to generate a mechanical vibration; and an input controller operatively connected to the main controller board, wherein the input controller is operable to control the vibration module. The combination of the two or more motors in the vibration module generates a multidirectional, multi-frequency vibration in a user. The main controller board automatically selects a frequency of vibration for each motor in the vibration module. The frequency of vibration of each motor is between about 5 Hz and about 500 Hz. The vibration module comprises two motors that vibrate perpendicular to one another (one is parallel to the body, the other perpendicular to the body). The vibration module further comprises a third motor that vibrates in an oblique direction to the other motors and to the body. The two or more motors vibrations are never synchronized. Each motor is driven through different sweeps of increasing or decreasing frequencies, increasing or decreasing power levels, and/or alternating with pauses, using randomized periods of time defined by the Fibonacci Sequence. The use of the frequency sweeps following a "jagged edge" progression (covering the full range of possible frequencies, differently with each motor) and the randomized length of time of the pauses between each frequency, forms a unique therapeutic model that is always different at each session and so prevents the nervous system habituation and constitutes one of the main element of the device therapeutic value. The input controller is an input device harness comprising at least two inputs. The at least two inputs are at least two dials connected to the main controller board. The device further comprising a power switch harness operatively connected to the power source. The device further comprising at least one sensor operatively connected to the vibration module. The at least one sensor is selected from an accelerometer, a heartbeat monitor, a pulse monitor, a temperature sensor, a humidity sensor, and a position sensor. The at least one sensor collects at least one data element. The at least one data element provides feedback for the multidirectional vibration. The at least one data element is stored in a database. The main controller board comprises at least one microprocessor, a voltage-regulated output, and an indicator LED. The main controller board comprises at least one non-transitory computer readable medium storing instructions for a data collecting interactive program which when executed by the at least one microprocessor, causes the at least one microprocessor to: receive input signals from the input controller, define a vibration frequency for each motor, and instruct each motor in the vibration module to generate the multidirectional vibration. The input controller is the interactive program. The input controller is operable to adjust the pulse width modulation of the vibration module. The pulse width modulation is adjusted between about 0% and about 100%. The pulse width modulation is adjusted between about 30% and about 100%. The vibration module is directly applied to the skin of a user. The device further comprising a transceiver operably connected to the vibration module and the main controller board. The transceiver is a Bluetooth™ or Wi-Fi transceiver. The device further comprising a magnet between the housing and the user. The device further comprising a conductive fabric to secure the device to the user or to secure at least one electrical capacitor to the vibration module. The device further comprising at least one electrical capacitor on the vibration module. The device comprises two or more vibration modules. A first vibration module and a second vibration module are set to a high frequency and a low power. A first vibration module is set to a high frequency and a low power and a second vibration module is set to a low frequency and a medium power with phasic pulsing. The motors within the vibration module provide vibration at both low frequencies and high frequencies. The vibration modules are placed on separate areas of a user's body. The vibration modules are placed bilaterally. The vibration module is located in an enclosure separate from the housing.

In an aspect, the disclosure further provides a method of using a vibrational therapy device comprising: placing at least one vibration module of the device of claim 1 at a location on a user; engaging a power switch harness to turn the device on; selecting a pulse width modulation for the vibration module using the input controller; and disengaging the power switch harness after a period of the to turn the device off. The main controller board comprises at least one non-transitory computer readable medium storing instructions for a data collecting interactive program which when executed by the at least one microprocessor, causes the at least one microprocessor to: receive input signals from the input controller, define a vibration frequency for each motor, and instruct the vibration module to generate the multidirectional vibration. The input controller is the interactive program. The input controller is operable to adjust the pulse width modulation and/or the amplitude of the vibration of the vibration module. The pulse width modulation is adjusted between about 0% and about 100%. The method further comprising receiving an input from a sensor to provide feedback to the vibration module. The device further comprises a magnet between the housing and the user. The method further comprising securing the at least one vibration module to the user using a conductive fabric with tribo-electrical capability. The device further comprises at least one electrical capacitor on the vibration module. The frequency of vibration of each motor in the vibration is automatically selected by the main controller board. The frequency of vibration of each motor is between about 5 Hz and about 500 Hz. The method further comprising placing a second vibration module on the user.

In another aspect, the disclosure provides a method of stimulating the autonomous or parasympathetic nervous system, the method comprising: placing a therapy device comprising at least one vibration module having two or more motors on the skin of a user; selecting a power level for the vibration module; and removing the vibration module after a period of time. The therapy device generates a random, non-repeating mechanical vibration.

The device further comprises a main controller board operable to automatically select a frequency of vibration for each motor in the vibration module. The frequency of vibration of each motor is between about 5 Hz and about 500 Hz. The vibration module comprises two motors that vibrate perpendicular to one another. The vibration module further comprises a third motor that vibrates in an oblique direction. Each motor is driven through different sweeps of increasing or decreasing frequencies, increasing or decreasing power levels, and/or alternating with pauses, using randomized periods of time defined by the Fibonacci Sequence. The at least one vibration module is placed near the vagus nerve. The therapy device is placed on the skin of the user for about 5 minutes to about 1 hour.

Additional embodiments and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF THE DRAWINGS

The description will be more fully understood with reference to the following figures, which are presented as various embodiments of the disclosure and should not be construed as a complete recitation of the scope of the disclosure, wherein.

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Disclosed herein is an electronic device which generates a combination of adjustable mechanical vibrations, a microcurrent, and a low level magnetic stimulation when worn against or applied to a portion of the body. In an example, the device generates a series of multiple brief, low-amplitude, simultaneous, mechanical frequencies (vibrations) organized in "jagged edge" sweeps interrupted by randomized pauses. The use of the frequency sweeps following a "jagged edge" progression (covering the full range of possible frequencies, differently with each motor) and the randomized length of time of the pauses between each frequency, forms a unique therapeutic model that is always different at each session and so prevents the nervous system habituation and constitutes one of the main element of the device therapeutic value. In this example, the device forms never-repeated harmonic vibrations delivered in multiple directions (parallel, perpendicular and oblique in relation to the body). Without being limited to any one theory, the unpredictability of the soft vibration (non-synchronized, multiple motors applied in 2 units, one on each side of the body) may help disrupt the pathological, self-destructive frequency patterns.

This systematic delivery of ever-changing mechanical vibrations may prevent habituation that happens with even-tempo vibrations or synthetic drugs. By being close (but not identical) to the specific electromagnetic identity of a given cell/tissue and the surrounding harmonics, these repeated vibrations unexpectedly helps the tissue rapidly restore ideal biological function, modulate inflammation, and diminish pain. Without being limited to a particular theory, this approximation and the brevity of each frequency/harmonic may prevent any of the dangers of a more precise resonance program by rarely or only briefly hitting the exact frequency of the tissue.

The device utilizes an asymmetrical weighted motor to generate mechanical vibrations within a range of biologically appropriate frequencies. Without being limited to a particular theory, the mechanical vibrations may desensitize an overactive and/or overstimulated nervous system. The mechanical vibrations may allow the user to return to a state of calm and alert relaxation. The device may further include an electrical micro-current and/or a weak electro-magnet that contribute to dissipating the effects further in the body. The device may also include at least one physiological sensor to collect physiological data from the user and provide feedback to the device, triggering some automatic, pre-set protocols or some adaptive protocols executed by an interactive program. For example, the adaptive protocol may be, but is not limited to, a vibration rhythm adjusted to the rhythm of the gait or triggered by some heart rate variability indicative of the onset of some form of stress.

The mechanical vibration generated by the device may be highly adjustable over a wide range of frequencies, pulse width modulation, and amplitude. The vibration can be adjusted by modulating the output frequency of the motors, by adjusting its strength via pulse width modulation, or by adjusting its amplitude. In addition to being adjustable, the device is highly consistent, allowing the user to generate the same pattern of vibrations again and again over subsequent applications of the device for specific protocols, or conversely generate randomized frequency sweeps that are always different in order to prevent habituation by the nervous system, which would limit its efficacy over time.

The device may be used to collect physiological data which may be used to feed an interactive program governing multiple therapeutic protocols. The device and interactive program may further provide synchronization of therapeutic protocols with an adequate program of personalized cognitive advice. The interactive program may deliver both preset protocols and individually adjusted protocols through its near-instantaneous interactive action. In an embodiment, the program may be a vibration program. In one embodiment, the personalized cognitive advice may be delivered through text messages. The interactive program may deliver a protocol in response to the data collected by the sensors placed in the vibration module.

In one embodiment, the device is worn against the skin or affixed to a piece of clothing that can transmit the vibrations, such as, but not limited to: a belt, or on a horse or dog, a collar, halter, girth, pad, etc. The device may be used with animals, such as humans, horses, dogs, or cats. The device may provide the following benefits: stress relief and emotional balance; muscle relaxation; rapid pain diminution and relief; reduction in addiction and/or addictive behaviors, as well as diminution of side effects and withdrawal effect when medicine dosing is reduced; building neurological memory used for the improvement of balance and symmetry of motion; and facilitation of mental, emotional, and physical training for humans and animals.

Reducing the hyperactivity of an overactive and/or over-stimulated nervous system may produce a calm, relaxed state of being, and also reduce the over-stimulated pain pathways contributing to many chronic pain syndromes. It also may be therapeutic for muscle and joint injuries and/or neuromuscular junction malfunctions that create a loss of function associated with the super-contracted state of muscles, such as spasms present in many medical conditions.

Once a state of relaxed calm and/or muscular de-contraction has occurred, a switch in the interactive program controlling the vibration module may allow it to pace the nervous system (and/or neuromuscular junction) at its proper biological frequency of operation resulting in improved coordination, balance, and fluidity of the movement of agonist/antagonist pairs.

Device

Figure 1:
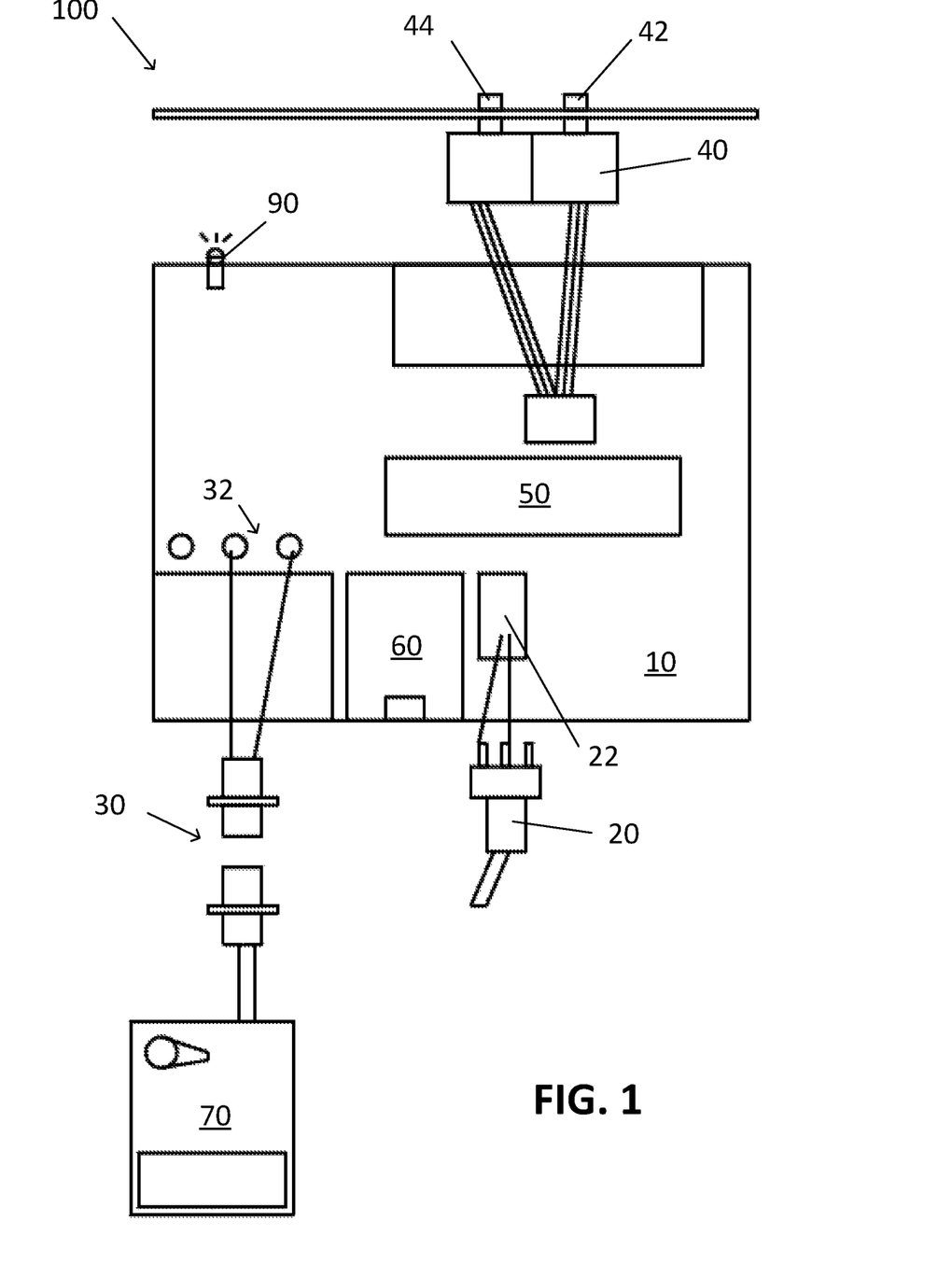
FIG. 1 is an illustration of the device in one embodiment.
Figure 2:
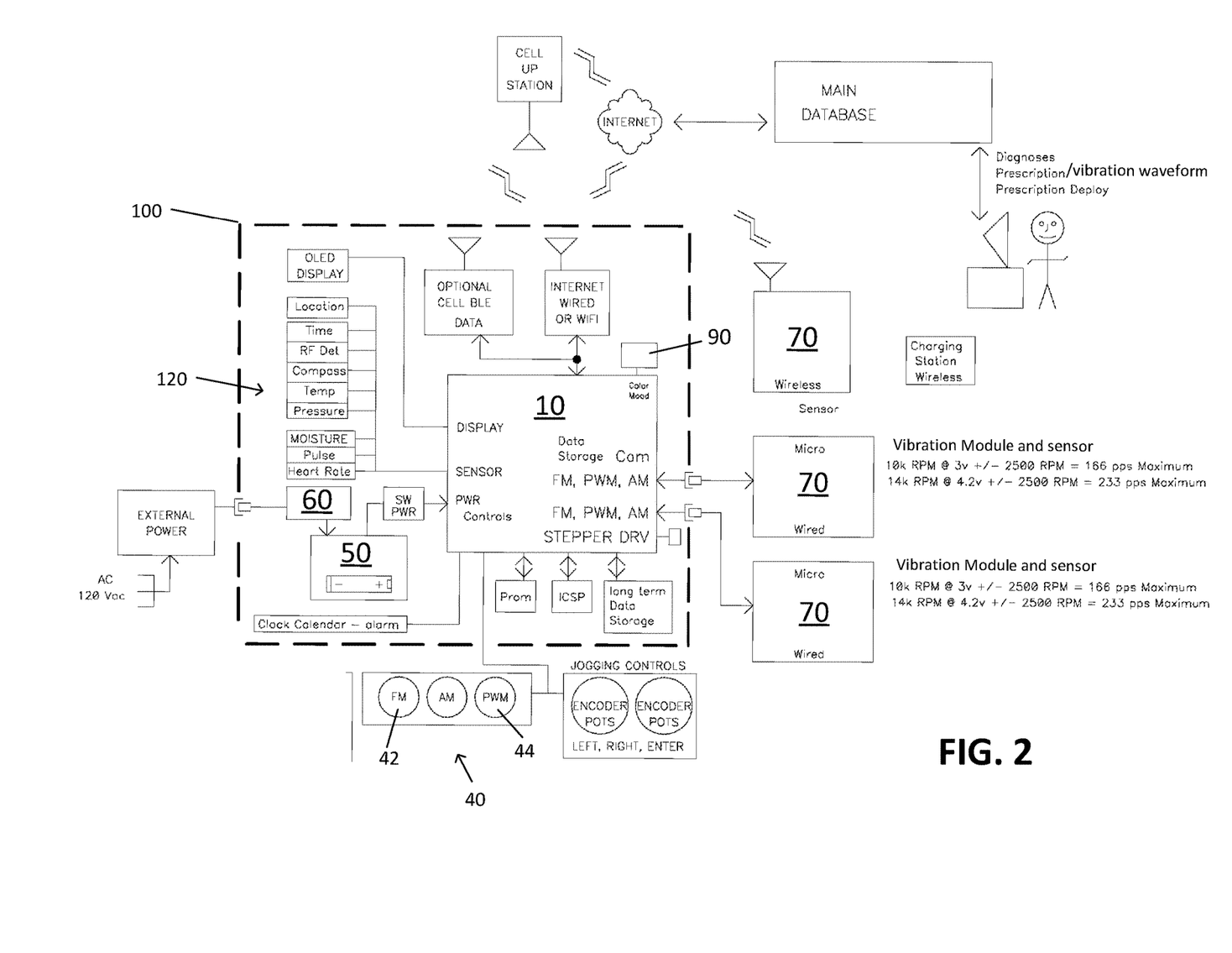
FIG. 2 is a schematic of the device in one embodiment.

As seen in FIGS. 1 and 2, the device 100 may include a main controller board 10, a power switch harness 20, an output jack harness 30, an input device harness 40, a power source 50, a battery charger circuit 60, a vibration module 70, and a transceiver 80. In various examples, the device may be small enough to be wearable on many different areas of the body during physical activity.

The main controller board 10 may include at least one processor, a voltage-regulated output, and a tri-color indicator LED 90. In some embodiments the processor is a microprocessor. A/D inputs to the microprocessor may be rationalized against a reference voltage of 4.096V. The device 100 may further include a housing 120. In an example, the main controller board 10 may be enclosed in a housing 120.

Figure 3A:
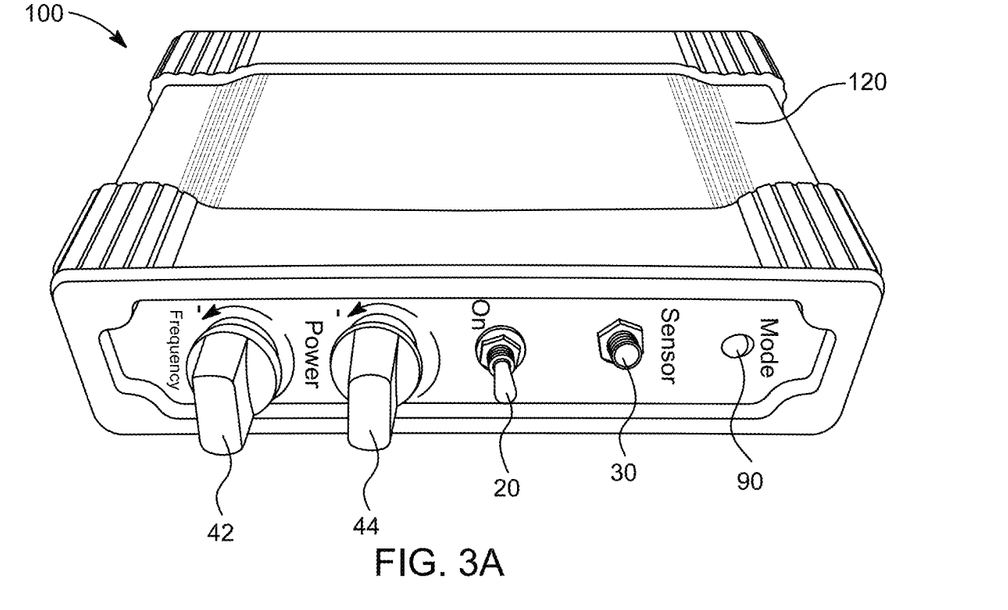
FIG. 3A is a front view of the device in one embodiment.

As seen in FIGS. 1 and 3A, the power switch harness 20 is a single-pole-double-throw toggle switch which is wired into the main controller board at 22 which toggles power to the vibration module 70 on and off. In an example, the power switch harness 20 is operatively connected to the power source 50 via the controller board 10. In an example, a red wire may be soldered to one of the outside terminals of the switch, and a black wire may be soldered to the middle terminal of the switch. In an embodiment, the power switch harness 20 may be a single pole double throw ON-ON toggle panel-mount switch. The following aspects of the power switch harness 20 can be changed without affecting how the device functions: mounting style, actuator length, electrical rating (provided it can handle at least 7.5 VDC @ 2A), illumination, and switching from SPDT to DPDT or 3PDT or 4PDT.

As seen in FIGS. 1 and 3A, the output jack harness 30 may be a male DIN power jack, which is wired into the main controller board 10 at 32. For example, the male DIN power jack may have a 2.5×5.5 mm diameter. In an embodiment, it is the mating connection point for the vibration module 70. In one embodiment, a red wire is soldered to the pin 1 terminal of the jack (in common with the center pin of the jack) and a black wire is soldered to the pin 3 terminal of the jack (in common with the shell of the jack). The output jack harness 30 may use any style of connector known in the art provided it matches the style used in the vibration module 70. In various examples, the output jack harness 30 may be used to connect at least one sensor and/or at least one vibration module to the controller board.

The input device harness 40 includes an input to adjust attributes of the vibration from the vibration module. In an embodiment, the input device harness may include a low-power display, such as an OLED display. In other aspects, the device may include a low-power display separate from the input device harness. As also seen in FIG. 3A, the input device harness may include two dials 42, 44 connected to the main controller board 10 for controlling attributes of the vibration to be generated by the vibration module 70. Non limiting examples of dials include potentiometers, rotary encoder switches, capacitive touch, and similar input devices. In one embodiment, the input device harness 40 may include 2 potentiometers, each with about 10 Kohms resistance. The resistance can be varied. The functions of the potentiometers can be reversed between each other. In one embodiment, turning either potentiometer counter-clockwise reduces the relevant value, turning it clockwise increases the relevant value. In other embodiments, this can be reversed. In some embodiments, the potentiometers may be rotary encoder switches. In other embodiments, the potentiometers may be an alternate input technology such as a touchscreen or a small joystick.

The input device harness 40 allows the user to adjust attributes of the vibration generated by the vibration module 70. Non-limiting examples of vibration attributes that may be adjustable by the user include frequency, amplitude, duty cycle, or pulse width modulation (PWM) of the motor. In one embodiment, the PWM may be referred to as the power. For example, the user may adjust the desired frequency and the desired pulse strength using the input device harness 40. In an embodiment, one dial 42 may be used to adjust the frequency of the vibration and a second dial 44 may be used to adjust the PWM. The frequency, amplitude, and duty cycle may be adjusted via 10-turn potentiometers. In an embodiment, the dials are each rationalized differently according to the minimum and maximum range of each input. In another example, the PWM may be set by the user and then the frequency may be automatically selected by the main controller board.

In some examples, turning a dial to the left decrease the value being adjusted, turning the dial to the right increases the value. In other examples, the values may be viewed and/or set through a user interface. The color of the LED 90 may be used to represent the setting and value of an attribute. For example, red may represent PWM, blue may represent frequency, and green may represent amplitude. The association of a color with an attribute may vary. The relevant LED color may be increased in intensity as the related value is increased.

The power source 50 supplies power to the main controller board 10. The power source may be an internal battery or an external power source. In an example, the power source 50 may be incorporated in the housing 120. In an embodiment, the power source 50 may be a battery which is held by standard battery clips. In various embodiments, the battery can be rechargeable or non-rechargeable. In one embodiment, the power source 50 is a 18650 size 3.7V 3000 mAh lithium-ion rechargeable battery. The power source may have a voltage ranging from about 2.5 V to about 5.5 V. In various examples, the power source may have a nominal voltage of at least about 2.5 V, about 3.6 V, about 3.7 V, about 3.8 V, or up to 5.5 V. In other embodiments, the power source 50 may be a bench-top power supply, provided that it is able to supply about 3.7V up to a maximum of about 0.5 A.

Figure 3B:
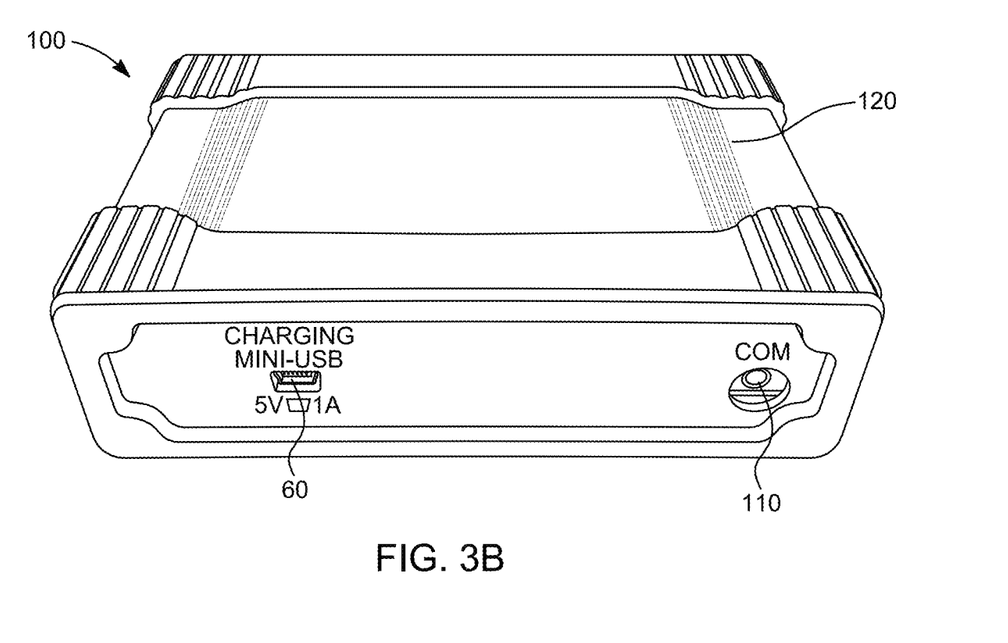
FIG. 3B is a rear view of the device in one embodiment.

The battery charger circuit 60 may be a circuit board which is wired into the main controller board 10 to allow connection to the power source 50. In one embodiment, the battery charger circuit 60 may accept up to 6 W of power via a standard USB Mini connector to charge the power source 50. The battery charger circuit 60 may use any style of connector known in the art, for example, as seen in FIG. 3B, it may be a USB Micro, 3.5 mm stereo or 2.1×5.5 mm DIN.

As seen in FIG. 1, the device may include one or more vibration modules 70. In an example, the vibration module 70 may be a pulse code modulator (PCM). The vibration module 70 includes more than one motor that generates vibrations when powered or commanded by the main controller board 10. In an example, each motor may be an asymmetrical weighted motor circuit or a stepping motor. In another example, the motor may be a driving motor that oscillates orbitally to generate vibrations which form the primary and beat frequencies. The motors may generate a wide range of primary frequencies, and the controller board may achieve beat frequencies by combining and alternating the function of the motors. In an example, the asymmetrical weighted motor may be an offset DC motor. The motor may rotate at least about 7,500 RPM at 3V to about 16,500 RPM at 4.2V. In specific embodiments, the motor may spin at about 10,000 RPM at 3V or at about 14,000 RPM at 4.2V.

The motors may be mechanically coupled to the surface of the vibration module 70. In some examples, the vibration module 70 may include two or more motors. For example, the vibration module may include 2 motors, 3 motors, 4 motors, 5 motors, or 6 motors. In an example, a system may include 2 vibration modules, each with 2 or more motors.

The vibration module 70 may produce multi-directional, multi-range, randomized frequencies of organized, never-repeated mechanical harmonics. The vibration module 70 may generate vibrations having frequencies ranging from about 0.0625 Hz to about 1500 Hz. The device may maximize the therapeutic effectiveness of the vibration module by driving each motor within a specific frequency range, allowing each source to achieve their own optimum frequency range relatively to their power usage. For example, frequency ranges for different motors may include 1 Hz to 50 Hz, 50 Hz to 100 Hz, 20 Hz to 70 Hz, 70 Hz to 150 Hz, and/or 150 Hz to 500 Hz. In various embodiments, the frequency may range from about 0.0625 Hz to about 5 Hz, from about 5 Hz to about 100 Hz, from about 50 Hz to about 200 Hz, from about 100 Hz to about 300 Hz, from about 200 Hz to about 400 Hz, from about 300 Hz to about 500 Hz, from about 400 Hz to about 600 Hz, from about 500 Hz to about 1000 Hz, from about 750 Hz to about 1250 Hz, and from about 1000 Hz to about 1500 Hz. In other embodiments, the frequency may be at least about 5 Hz, at least about 50 Hz, at least about 100 Hz, at least about 200 Hz, at least about 300 Hz, at least about 400 Hz, at least about 500 Hz, at least about 750 Hz, at least about 1000 Hz, and at least about 1500 Hz. In additional embodiments, the frequency may be less than or equal to about 5 Hz, less than or equal to about 50 Hz, less than or equal to about 100 Hz, less than or equal to about 200 Hz, less than or equal to about 300 Hz, less than or equal to about 400 Hz, less than or equal to about 500 Hz, less than or equal to about 750 Hz, less than or equal to about 1000 Hz, and less than or equal to about 1500 Hz. In one embodiment, the frequency may be about 200 Hz to about 250 Hz. In another embodiment, the frequency may be less than 80 Hz. In some examples, low frequency may refer to less than 150 Hz. In at least one example, low frequency refers to about 5 Hz. In other examples, high frequency refers to greater than 150 Hz. In at least one example, high frequency refers to 250 Hz to 500 Hz.

The amplitude or intensity of the stimulation may be calibrated at the time of manufacture by adjusting the voltage supplied to the motor to the optimum level specified for that motor by the manufacturer. The vibration, or stimulation, can be constant or it can be varied by means of an interactive program. In some examples, the power supplied to each motor may vary. For example, each motor be supplied a voltage ranging from about 1 V to about 4.5 V. In various examples, each motor may be supplied a voltage of at least about 1 V, 2.5 V, about 3.6 V, about 3.7 V, about 3.8 V, or up to 4.5 V. In various examples, the user may input and/or adjust the PWM (power) of the vibration module. The range of PWM may be about 0% to about 100%. In various embodiments, the PWM may be at least about 5%, at least about 10%, at least about 20%, at least about 30%, at least about 40%, at least about 50%, at least about 60%, at least about 70%, at least about 80%, at least about 90%, or at least about 100%. In additional embodiments, the PWM may be less than or equal to about 5%, less than or equal to about 10%, less than or equal to about 20%, less than or equal to about 30%, less than or equal to about 40%, less than or equal to about 50%, less than or equal to about 60%, less than or equal to about 70%, less than or equal to about 80%, less than or equal to about 90%, or less than or equal to about 100%. In some examples, low power refers to less than 50% PWM. In other examples, high power refers to greater than 50% PWM. For safety purposes to prevent a user from starting out at high power, the PWM for the vibration module may start at about 30% and increase incrementally over time. For example, the PWM may increase by 5% each time the device is used.

The biological systems that control molecular, cellular, and synaptic activity generally may move or activate asynchronously to one another; therefore, driving vibratory sources in a regular, synchronous pattern would be very different from the movement of biological systems. Without being limited to any one theory, driving vibration modules asynchronously to each other, and altering the window of time during which any particular vibration module is driven, will more closely mimic the apparent randomness by which biological systems move or activate and increase the effectiveness of the stimulation generated.

In an embodiment, each vibration module may include two or more motors to provide random vibration in more than one direction. Each motor may have its own specific timing sequence between changes of frequency. In an example, each motor of the vibration module may have a frequency range that it will vibrate within, and a specific window of time during which it will be driven. For example, in a vibration module that includes a total of 3 motors (A-C), the frequency range assignments may be: A: 2-4 Hz, B: 47-50 Hz, and C: 75-77 Hz. In another example, motor A may operate in the range of 1-50Hz, motor B may operate in the range of 50-100 Hz, and motor C may operate in the range of 100-250 Hz. In another example, the device may include a second vibration module that includes 3 motors (D-E), operating in the range of D: 20-70 Hz, E: 70-150 Hz, and F: 150-450 Hz.

The vibrations of the two or more motors may not be synchronized. In order to create the greatest number of harmonics while using the least amount of battery energy (to prolong the duration between recharges and to prevent heat accumulation), motors may be on during specific times and off the rest of the time. In some examples, software may be used to randomize the pause time between each frequency delivery. For example, one motor may be driven at a time, multiples of "Y seconds," and the multiple of "Y seconds" may be guided by the Fibonacci Sequence. For example, A may be driven for 1Y seconds, B would be driven for 1Y seconds, C would be driven for 2Y seconds, A would be driven for 3Y seconds, B would be driven for 5Y seconds, C would be driven for 8Y seconds, then A would be driven for 1 second and so on. Alternately, multiple motors may be driven at a time, each for varying multiples of "Y seconds;" for example, driving A for 1 second starting at the same time that B is driven for 2 seconds, after which C is driven for 3 seconds. In addition, the power applied to each motor may be changed or randomized such that the intensity of the vibration from each motor is varied.

The two or more motors in the vibration module may vibrate in different directions, such as allowing the device to optionally generate vibrations that are parallel, oblique, and perpendicular to the body to which it is applied. The device may also be configured to drive one or more motors in only one of these orientations. The combination of the two or more motors may create the vibration of the vibration module. For example, one motor may vibrate in the direction perpendicular to the skin and a second motor may vibrate parallel to the skin when the vibration module is applied to the skin of the user. Without being limited to any one theory, vibrations parallel to be body may affect the nervous system (e.g., vagus nerve stimulation, relaxation, pain relief, etc.) and increase retention of new nervous pathways (stimulation of the amygdala). Vibrations perpendicular to the body may be used to stimulate/educate the body and help the development of new muscles memories, with more immediate effect but less long term effects. Not being limited to any particular theory, the combination of multidirectional vibrations (parallel, oblique, and perpendicular) may produce quick, long lasting, and cumulative results. Again, without being limited to any one theory, mechanically activated Piezo 1 and 2 ion channels may respond to mechanical forces along the plane of the cell membrane (tension parallel to the cell membrane), and their activation may be tuned by various tensions and geometries of the cell surface. The configuration of the motors may apply vibrations parallel to the skin, as well as perpendicularly and obliquely. The multiple angles of the motors may provide multiple parallel vibrations to the piezo cells, however they may be situated in the body.

Without being limited to any one theory, when the device is configured to run vibration modules and/or motors in more than one orientation, it may be suited to stimulate mechanical ion channels. Mechanically activated piezo ion channels are believed to respond to mechanical forces along the plane of the cell membrane (tension parallel to the cell membrane), and their activation may be tuned by various tensions and geometries of the cell surface. Without being limited to any one theory, the unique configuration of a system with more than one vibration module to apply vibrations parallel to the skin, as well as perpendicularly and obliquely (left to right in one device and right to left in another) and are uniquely poised to take advantage of this particular property of piezo proteins. The multiple angles of the vibration modules provide multiple parallels vibrations to the piezo cells (however they are situated in the body).

Figure 4:
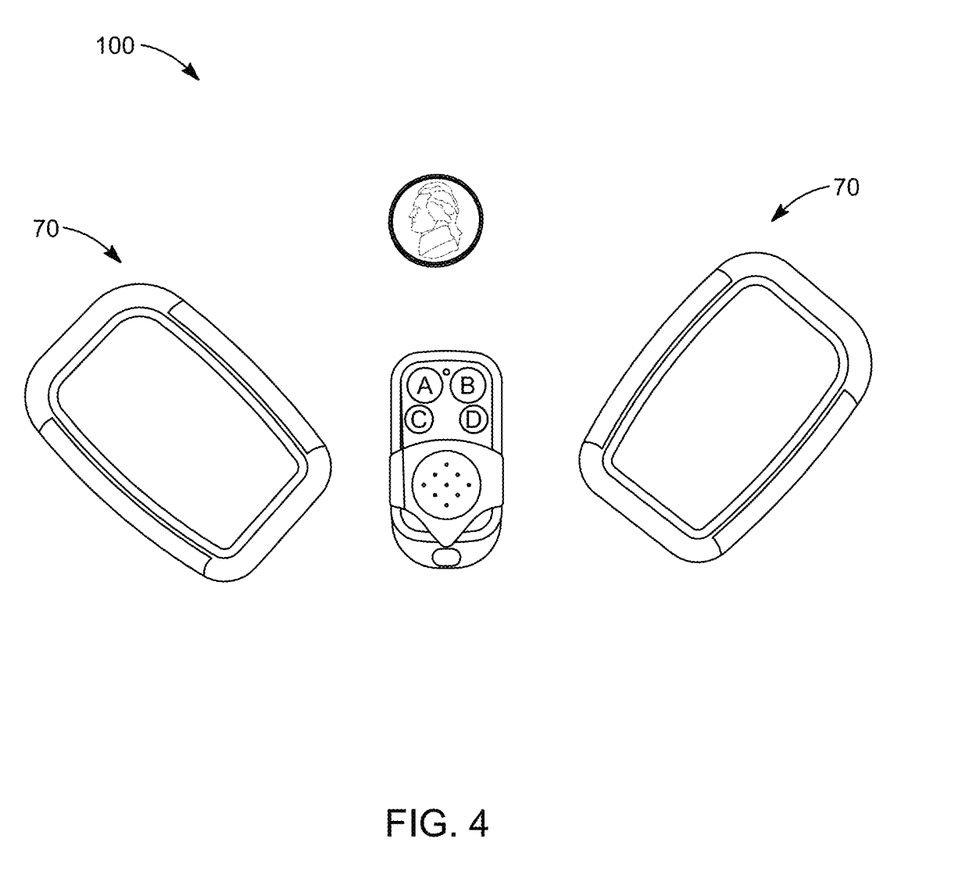
FIG. 4 is a view of the device with two vibration modules in one embodiment.

In various embodiments, the device 100 may include more than one vibration modules 70, for example, as seen in FIG. 4. For example, the device may include at least 1, at least 2, at least 3, at least 4, at least 6, or at least 8 vibration modules. The controller board 10 may drive one or more vibration modules, simultaneously or alternately, according to internal settings. Those settings can be reprogrammed in-circuit, as can the core software employed by the controller board.

In some examples, two vibration modules may be placed on both sides of the user's body (left-right), creating bilateral stimulation by delivering two sets of sensory stimuli (mechanical/tactile) occurring in multiple, rhythmic left-right patterns, always different of each other. The use of multiple vibration modules may produce a multiplicity of the arhythmical patterns. Without being limited to any one theory, the use of multiple vibration modules may prevent physiological habituation as well as mental focus on negative physiological events (pain, etc.). In an example, the main controller board 10 can control several vibration modules at the same time and deliver harmonized protocols applied to both legs for humans and 4 legs for animals. Further provided herein is a system that includes one or more devices.

The vibration module 70 is the part of the device that is directly applied to the skin of the user. In some embodiments the vibration module is within the same housing 120 as the main controller board 10. In other embodiments, the vibration module 70 is in a separate enclosure from the housing of the main controller board 10. For example, as seen in FIG. 4, the controller board may be within a remote, while the vibration modules may be in separate housings. The vibration module 70 may use any style of connector known in the art to connect to the main controller board 10 provided it matches the style used in the output jack harness 40. In an embodiment, the vibration module 70 connects to the main controller board 10 via a female DIN 2.5×5.5 mm power jack. In other embodiments, the vibration module 70 uses a wireless transceiver to connect to the main controller board 10. The housing of the vibration module may further be lined with negatively charged tape, such as Kapton® tape.

The transceiver may 80 connect the vibration module 70 with the main controller board 10 in order for the vibration module 70 to be cordless and independent from immediate proximity to the main controller board 10. The transceiver may be radio receptors/emitters. In an example, the transceiver 80 may be a Bluetooth™ or Wi-Fi transceiver. When communicating wirelessly, the transceiver may use a range of radio frequencies, from 315 MHz to 915 MHz. In some examples, the transceiver may use on-off keying (OOK) utilizing amplitude shift keying (ASK) on the 433 MHz frequency band by default.

In other examples, the device may be wired to communicate. When communicating in a wired format, the device may use either USB or a standard serial interface. In at least one example, the device may include USB by default.

The device may further include a communications port 110 for monitoring the state of the device. In one embodiment, the state of the device may be reported to a PC terminal window via the use of an on-board standard RS-232 communications port 110. In another embodiment, the communications port may be a Bluetooth or Wi-Fi transceiver.

The device may include at least one sensor 120. In various embodiments, the sensor 120 may include, but is not limited to an accelerometer, a heartbeat sensor, a pulse sensor, a temperature sensor (ambient or surface), a humidity sensor, a skin conductivity sensor, a location sensor, a GPS, a compass, a time sensor, an RF detection sensor, a pressure sensor, an atmospheric pressure sensor, a magnetic field density sensor, a heart rate monitor and IR sensors. In some examples, the sensors may use ultrasound technology. In some examples, the sensors may be added to the device utilizing an I2C (inter-integrated circuit) communications bus. In various embodiments, the device includes at least 1, at least 2, at least 3, at least 4, at least 5, or at least 6 sensors. The device may include more than one of the same sensor. The sensor can connect wirelessly with either device or a cell phone with a sensor application. Both the sensor application and the device are capable of reading various data points from the sensor. Non-limiting examples of data that may be received from the sensor include heart rate, pulse, ambient temperature, user temperature, humidity/moisture levels, atmospheric pressure, location, GPS data, time and date information, and frequency of use.

In an embodiment, the sensor 120 may have a small amount of storage space so that it can run one set program without the direction of either the app or the base unit. The sensor application or interactive program on the main controller board will record all data points received from the sensor in a database. The sensor may connect to the Internet, either through a phone app, a web page that connects to a database or directly to a database. The database will track all data points along with the particulars of the user (age, gender, medical conditions, etc.). As data is accumulated in the database, trends may emerge to allow the interactive program or sensor application to recommend vibration ranges or vibration sweeps that the user can select from, so that they do not have to be dialed in by hand. It may also allow for the detailed study of the medical uses of the device.

In an embodiment, the vibration module and any related programming may be triggered by a measurement from at least one sensor. In an embodiment, no action is required by the user once the device is in place and activated. For example, timing may be important when the device used as a vagus nerve stimulator to assist with relaxation and pain relief. Without being limited to any one theory, activation of the device without user input may avoid the complete flaring of the problem and may rapidly create a new neurological memory that does not include pain and/or anxiety. In an example, quick device response may shorten treatment duration, reduce noise, and increase the usage of the battery charge over time (a 30 s effective treatment used at the right time, versus a 20 min routine treatment that may be less effective because it will not be used exactly at the right moment).

In an embodiment, an accelerometer may be connected to the vibration module 70. The accelerometer measures the movement of the user, including but not limited to locomotion. Each accelerometer may measure up to 3,000 markers per second. In some embodiments, the device may include 3 accelerometers that read back/forth, up/down, left/right amplitude of movements. The data from the accelerometer provides feedback to the device and may be stored in the database. For example, frequency of the motor may be increased if a deceleration is measured by the accelerometer.

In an embodiment, a heartbeat monitor may be connected to the vibration module 70. The heartbeat monitor measures the heartbeat of the user. The data from the heartbeat monitor provides feedback to the device and may be stored in the database. For example, the frequency or the PWM may be adjusted based on a measured heartrate. In an embodiment, the interactive program may use the heartbeat data to initiate or adjust the vibration.

In an embodiment, a pulse sensor may be connected to the vibration module 70. The pulse sensor measures the pulse rate of the user. The data from the accelerometer provides feedback to the device and may be stored in the database. For example the frequency of the PWM may be adjusted based on the measured pulse. In an embodiment, the interactive program may use the pulse data to initiate or adjust the vibration.

In an embodiment, a temperature sensor may be connected to the vibration module 70. The temperature sensor measures the temperature of the environment. The data from the accelerometer provides feedback to the device and may be stored in the database. For example, the frequency or the PWM may be adjusted based on the measured temperature.

In an embodiment, a humidity sensor may be connected to the vibration module 70. The humidity sensor measures the humidity of the environment. The data from the accelerometer provides feedback to the device and may be stored in the database. For example, the frequency or the PWM may be adjusted based on the measured humidity. The humidity or moisture measured on the skin of the user may affect the conductance of the user's skin. Therefore, the interactive program may adjust the vibration based on the measured humidity at the user's skin.

Further provided herein is at least one non-transitory computer readable medium storing instructions for a data collecting interactive program which when executed by the at least one processor, causes the at least one processor to: receive input signals from the input device harness and any physiological sensors, define a vibration, and instruct the vibration module to generate the vibration. In other embodiments, at least one non-transitory computer readable medium may cause a processor on the user's smartphone to execute the interactive program. In one embodiment, the interactive program is executed by the microprocessor on the main controller board 10. In several embodiments, the interactive program may read and interpret the state of the input device harness 40, read and interpret the input received from any sensors present, define the attributes of the vibration to be generated, instruct the vibration module 70 to generate the desired vibration, display the state of the input device harness 40 by changing the color of the on-board tri-color LED indicator 90, or report the state of the device to a PC terminal window via the use of the communications port 110.

The interactive program may define at which frequencies and pulse widths the vibration/stimulation will be generated and for what duration of time. The interactive program may define the attributes of the vibration using a relative intensity curve for a continuous phase. In various embodiments, the interactive program may control frequencies on the motors of the vibration module of about 5 Hz to about 1500 Hz. This control may allow the delivery of very specific protocols, using an infinitely randomizing program. In other embodiments, the interactive program may utilize randomization to create the vibration. When the device includes more than one vibration module, a phasing mode in the interactive program may be used to alternate vibration between the vibration modules.

The interactive cognitive program or database may include a library with different folders specific to each condition, in particular in the area of behavior modification and addiction reduction. Non-limiting examples of different conditions include anger management, chemical addictions, social phobias or anxieties, OCD behaviors, etc. The punctual occurrence of these issues is usually preceded by a moment of anxiety that translate in an increase of cardiac pulse. In an embodiment, the device may detect the increase in pulse from a heartbeat monitor or pulse sensor in the device. If the pulse is above a threshold value, or if the pulse increased by a threshold percentage, the interactive program may start the device in a calming mode.

The library of advice and recommendations may be stored in the cloud. In an embodiment, the desired cognitive messages from the library can be delivered to user at the appropriate time. For example, the cognitive messages may be delivered to the user through SMS messages in the form of text, images, vibrational sounds, spoken messages, subliminal messages, or combinations thereof. These cognitive messages, selected by user out of the library, may reinforce the ongoing improvement of the user's behavior, such as physical, emotional, or neurological behavior. In one example, the behavior may be pain management.

The device or vibration module can be affixed to the user with fabric or heavy duty, wide tape (athletic or otherwise) anyplace on the body. In various embodiments, the device may be attached to the user with a compression fabric. The compression fabric holds the device or vibration module tightly against the user's skin. In one embodiment, the compression fabric is a conductive/spacer fabric with air flow capability. The conductive compression fabric may apply gentle, uniform pressure to the body while preventing body heat and vibrator heat accumulation. In an example, the conductive fabric may act as an electrical capacitor and may produce triboelectricity on contact with the skin. Without being limited to any one theory, the triboelectrical charge may be amplified by the device vibrations (up to 2,500V in milliamp intensity) and may increase any therapeutic effects of the device. For example, use of the conductive fabric in combination with the at least one vibration module of the device may multiply the therapeutic effect of the device by a factor of 2 or 3.

In some examples, the conductive fabric may comprise, but not limited to, silver, copper, carbon, or combinations thereof. The conductive fabric may also include polyvinyl chloride (chlorofibers). Chlorofibers may create a stable negative electrostatic charge by friction, vibration or scraping of any nature, even in near saturated dampness conditions.

The device, and/or the vibration module, may be surrounded by insulation. In one embodiment, the device may be used with a conductive fabric that is applied tightly directly on the vibration module insulation as well as an under-garment worn by the user. In one example, the under-garment may be animal clothing in the case of animal therapy. The connection between the vibration module insulation and the skin is insured by the dry conductive fabric. In some embodiments, the conductive fabric may also act as a capacitor by storing static electricity created by the user and the vibration module. In an embodiment, the compression fabric may distribute any micro-currents across a larger surface area than the device or vibration module alone.

In one embodiment, the device may include a covering hood made of pure silver stretch fabric. The covering hood may act as a dry electrode on contact with the skin. The hood may be lined with a pure copper fabric. Without being limited to a particular theory, the contact between the silver and the copper fabrics may create a thermopile that increases the electrical output of the device. In an embodiment, the hood may include a second liner forming a pocket on each side of the hood covering the vibration module. In an embodiment, the hood may be made of several thicknesses of chlorofiber fabric. Without being limited to a particular theory, the chlorofiber fabric may have the ability to produce negative polarity friction electricity (tribo-electricity), regardless of the polarity of the materials contained by it.

The device may further include an electrical capacitor connected to the vibration module. For example, an electrical capacitor may be placed on one side of the vibration module. In an embodiment, the electrical capacitor is on the side of the vibration module directed away from the user. In one embodiment, the capacitor may be composed of several sheets of paper alternating with card stock. Every other layer may be covered by an insulator. The insulator may be an insulating film (e.g. Kapton™ or Teflon). A larger mass (such as, but not limited to polyurethane foam) can be used to produce a larger electrical charge (of either polarity), that will be transformed into a negative charge by the chlorofiber on the next-to-the-skin surface of the fabric. The greater the surface of the insulating film and the greater the mass of the fabric/foam construction, the greater the charge. For example, 4 papers of ½ square inch each×2 sides=4 inches of insulating film surface. The separation produced by one thickness of card in between 2 sheets of paper lined with insulating film may be sufficient to render each side of insulating film covered paper electrically active on its own. In various embodiments, the level of negative electricity produced by the chlorofiber fabric and stored by the electrical capacitor may be at least 1,000V, at least 1,500V, or at least 2,000V on the surface of the insulating film. The card stock and paper that form the capacitor may be printed on both sides with words such as Love, Heal, Cure, Soothe, etc. in 45 languages, over several layers of ink applied in all sizes and directions.

The chlorofiber fabric electrical charge is always negative and can be further increased by the application of a coating of Polytetrafluoroethylene (PTFE)—a synthetic fluoropolymer of tetrafluoroethylene (ex. Teflon). The conductive copper/silver/carbon fabric (or weaved-in/knitted-in yarn) will discharge it when put in contact with the user's body. In an embodiment, the device's vibrations may reinforce and increase the tribo electricity effect.

In additional embodiments, the device may further include a magnet between the user's skin and the vibration module. In other embodiments, the magnet may be between the conductive fabric and the vibration module. In an embodiment, the magnet is a rare earth magnet. The device may further include a barrier between the magnet and rest of the device to reduce the effect of the magnetic field on the other components of the device. The device vibrations and tribo-electricity generated by the conductive fabric may work together to deliver a combination of localized mechanical vibrations, static electric fields from the tribo-electric effect of the chlorofibers of the conductive fabric, and weak magnetic fields from a small rare earth magnet. Together these components may deliver a therapeutic effect greater than each individual component used separately.

In one embodiment, a magnetic capacitor may be placed on the opposite side of the vibration module from the electrical capacitor. For example, the magnetic capacitor may be placed inside pocket on the hood. In order to protect the motor inside the vibration module from the magnetic field created by the magnet, the field has to be diffused away from the motor and turned toward the user. In one embodiment, this may be achieved by using a piece of sheet metal shaped like a cup (for instance like a beer bottle cap). In an embodiment, the magnet, on top of an electric capacitor, may be placed in the concave side of the cup. The north pole of the magnet (negative pole) is turned toward the user. In an embodiment, if the walls of the cups are turned inward (about 10 to 20 degrees), the entire magnetic field may be focused onto a narrow surface and concentrated. This may be useful for a localized treatment, such as acupuncture. In another embodiment, if the walls of the cup are turned outward (about 1 to 60 degrees), the entire magnetic field may be diffused to a larger area of the body through the surface of its sharp edge. As a result, the power of the magnet may be diminished by up to about 90% on its south side.

In an embodiment, tribo-electricity may be created by movement, such as rubbing or vibrations. For example, when the device is turned on, the vibrations activate the micro-current and micro-magnetic field and they may be amplified. The negative electric charge created may be applied to the body through the contact of the hood cover that works as a "dry electrode".

Methods of Using the Device

Provided herein are methods of preparing the device for use and treatment of a user by applying the device to the skin of a user. In various embodiments, the device may use high frequency and low power to promote relaxation, which may act more on nerves, or low frequency pulsing to activate the muscle.

The main controller board 10 regulates all aspects of the device's operation. It takes power from the power source 50, examines the state of the input device harness 40, reads input from the one or more sensors, then uses the output jack harness 30 to drive the vibration module 70. The method of preparing the device for use and using the device may include checking that the power switch harness 20 is set to the "off" position, adjusting the input device harness 40 to approximate the desired vibration, applying the vibration module to the skin of the user, setting the power switch harness to the "on" position, observing that the tri-color indicator LED on the main controller board 10 activates, observing that the vibration module 70 has begun generating the vibration, adjusting the input device harness 40 as needed to modify the vibration, and setting the power switch harness 20 to the "off" position when finished. If at any time the device loses power and deactivates, the power source 50 may need to be replaced or recharged via the battery charger circuit 60.

The device is turned on or off by toggling the power switch harness 20. The battery charger circuit 60 accepts up to 6 W of power and uses it to charge the power source 50. If the charge available from the power source 50 is deemed by the battery charger circuit 60 to be too low, the battery charger circuit 60 disables the device in order to protect the power source 50. The vibration module 70 is applied to the target user location and, when driven by the main controller board 10, generates the vibration defined by the user's adjustment of the input device harness 40.

The device may be used to provide therapy or be used in combination with therapy to a user. In an embodiment, the device may be used alone or in combination with manual Endotapping™. The therapy provided by the device may include mechanical vibrations, static electric fields, weak magnetic fields, and combinations thereof. In an embodiment, the therapy may be a combination of a calming effect in response to a physiological change and a cognitive message, both delivered simultaneously in a very moment it is needed.

The device may be used for therapy or treatment of a condition affecting the user by providing a non-invasive mechanical stimulation to the body. In some examples, the device may be used as an autonomic/parasympathetic nervous system stimulator. In an example, the vibrations produced by the device may be non-nerve-specific, non-habit-forming (due to the continuous randomization of its action), biologically interactive and adaptable (through the associated sensors and software). Without being limited to any particular theory, the device may achieve results via stimulation of mechanoreceptors (nerve endings which detect mechanical stimulus such as movement or pressure) rather than interfering with the transmission of pain messages via nociceptors. In an example, the device may be a non-invasive mechanical vagus nerve stimulator. Non-limiting examples of conditions for therapy or treatment include pain, neuropathies, sciatica, cancer pain, arthritis, post-surgical migraine, backache, phantom limb pain, numbness and tingling, general relaxation, anxiety, ADHD, stress, muscle spasms/tremors, sleep, resetting of neuronal activity, stroke, fibromyalgia, narcotic dependence, depression, voice/swallowing, bowel movements, breathing, sleep apnea, and obsessive-compulsive behaviors. Animals may have behavior changes (aggression, anxiety), pain reduction, or biomechanical modification after using the device for a period of time. For muscular issues, such as treatment of stroke or athletic training, the use of the device may be combined with specific concentric or eccentric exercises. Exercise may be synergistic in boosting the efficacy of device, especially for neuro-muscular conditions. Without being limited to any one theory, the device may have an effect on emotional stress, including but not limited to a relaxation effect including decreased physiological arousal; increased attentional flexibility; distancing effect; and/or decreased worry over future events.

The vibration module may be placed either onto an area afflicted with pain or a general nerve meridian or trigger point. These often coincide with the location of physiologically relevant nerve centers such as the trigeminal nerve of the face (implicated for migraine treatment) or the vagus nerve (implicated for the treatment of epilepsy, sleep, or digestion issues). Non-limiting examples of locations on the body where the vibration module may be placed for pain treatment or relaxation include the trigeminal nerve, the vagus nerve, the sternum of the chest, the lower back, the base of the spine around the sacroiliac joint, the base of the neck, between the shoulder blades, the base of the skull, behind an ear, alongside the carotid artery and vagus nerve of the neck, along the cheek bones or under the eye or next to the nose to stimulate the trigeminal nerve, skull bones just behind the ear to activate the motor centers deep in the center of the brain stem, on the arm or muscle, or the bottom of the foot to stimulate nerve endings (for example, as determined by the user having a "tingling" sensation travel along the leg towards the hips). In an embodiment, the device may be applied to either the belly of the muscle or the ends (insertion points) of the muscle. The vibration may be applied at the start of a movement, during the middle of a motion, or to the antagonist muscle during the motion (e.g. closing the arm so that instead of vibrating the bicep (agonist), the tricep (antagonist) is being vibrated to promote relaxation and lengthening of the range of motion of the muscle.

For pain treatment and general relaxation, a higher frequency may be used with a low to medium power/PWM setting. In an embodiment, the power/PWM may be estimated by the user adjusting the power until the vibration is felt by the user and determined to be acceptable. In one embodiment, the frequency used for pain treatment and general relaxation may be about 200 to about 250 Hz.

In some embodiments, the device may include two or more vibration modules. In an embodiment, the device may include two vibration modules, either both set to high frequency and low power or one at high frequency and low power and the other set to low frequency and medium power with phasic pulsing. The vibration modules may be placed upon painful trigger points for the treatment of fibromyalgia pain and muscular cramping. In some embodiments, the device with two vibration modules may be combined with eccentric exercises targeting the most affected and painful joints of the body. For stroke treatment, one vibration module may be set to high frequency low power and the other vibration module may be set to phasic pulsing. In this embodiment, the vibration modules may be placed upon the belly of the muscle being rehabilitated. The vibration may be applied by the vibration module for about 20 minutes. In an embodiment, the user may improve regained muscular control and coordination during voluntary movements after use of the device for about 20 minutes.

The vibration may be applied to the user for a period of time ranging from about 20 seconds to about 10 hours. For example, the vibration may be applied for about 2 minutes to about 10 minutes, about 5 minutes to about 15 minutes, about 10 minutes to about 20 minutes, about 15 minutes to about 30 minutes, about 30 minutes to about 60 minutes, about 1 hour to about 5 hours, and about 5 hours to about 10 hours. In various embodiments, the vibration may be applied for at least about 2 minutes, at least about 5 minutes, at least about 10 minutes, at least about 15 minutes, at least about 30 minutes, at least about 60 minutes, at least about 2 hours, at least about 5 hours, at least about 8 hours, and at least about 10 hours. In additional embodiments, the vibration may be applied for less than or equal to about 2 minutes, less than or equal to about 5 minutes, less than or equal to about 10 minutes, less than or equal to about 15 minutes, less than or equal to about 30 minutes, less than or equal to about 60 minutes, less than or equal to about 2 hours, less than or equal to about 5 hours, less than or equal to about 8 hours, and less than or equal to about 10 hours. In an embodiment, the vibration may be cycled more than one time, with a period of rest between cycles.

Figure 5A:
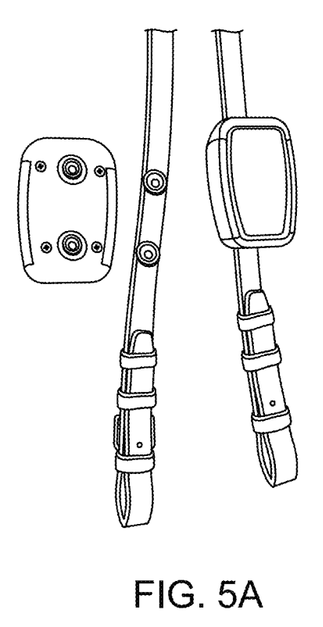
FIG. 5A is a view of the device with two vibration modules on horse riding reins in one embodiment.
Figure 5B:
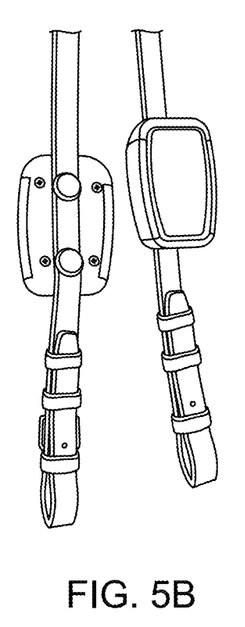
FIG. 5B is a view of the device with two vibration modules on horse riding reins in one embodiment.
Figure 5C:
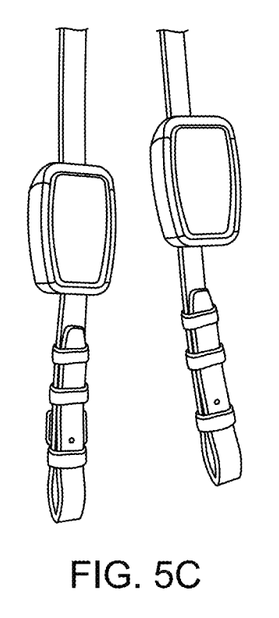
FIG. 5C is a view of the device with two vibration modules on horse riding reins in one embodiment.

When multiple vibration modules are used, the vibration may be applied in multiple vibration phases on alternating vibration modules. In an embodiment, a vibration phase may run for about 2 minutes. Each phase may be repeated for at least 2 or 3 cycles for a total running time of at least about 4 minutes to about 6 minutes. For example, where there are 2 vibration modules on the front legs of an animal such as a horse or 2 locations on a human body, the vibration modules may alternately cycle between a first phase with about 10 seconds of rest, 20 seconds of sharp, separated pulses in the rhythm of the gait, and 10 seconds or rest and a second phase of 10 seconds of rest, 20 seconds of continuous, progressive vibration, and 10 seconds of rest. In another example, where there are 4 vibration modules on a horse, the vibration modules may be alternatively cycled between the first and second phases. For example, FIGS. 5A, 5B, and 5C show 2 vibration modules on horse riding reins. The purpose of this placement is to vibrate the mouth of the horse and the hands of the rider by vibrating the leather reins. The same method of attachment may be used for a horse halter or a head halter, a saddle girth, etc.

The device and/or vibration module may be placed at any position on the user. For behavior modification of a horse, one vibration module may be placed in an easy-to-use location, for example under a surcingle, under the headpiece of a halter, or under the middle of a girth. For biomechanics modification, vibration modules may be applied in pairs, as follows below. For balance issues, vibration modules may be applied on each side of the underside of the neck, for example, on a breast plate. For gait development or gait unevenness correction, a vibration modules may be applied on the back of the front leg forearm (anterior flexor muscle), and additionally on the front of the hind leg gaskin. For back soreness, vibration modules may be applied on each side of the spine under a saddle pad but not directly under the saddle when riding or under a surcingle when lunging. For localized pain, vibration modules may be applied wherever the spasm is evident, for example, on the gaskin for "shivers" or on the croup near the sacroiliac joint with a compression bandage or an adhesive tape.

In various embodiments, more than one vibration module may be included in the device and placed at multiple locations on the user. In one embodiment, the device includes 2 vibration modules. In an example, the vibration modules may be located on the left and right forearms. In another embodiment, the device may include 3 vibration modules. In an example, the vibration modules may be located on the left and right forearms and the middle of the chest under the girth. In another embodiment, the device may include 4 vibration modules. In an example, the vibration modules may be located on the left and right forearms and the left and right gaskins, above the hock. In another embodiment, the device may include 6 vibration modules. In an example, the vibration modules may be located on the left and right forearms, the left and right gaskins, above the hock, and 2 on the back of the shoulder blade at the top, under the edge of the saddle pad.

In another example, one or more vibration modules placed on the horse's legs and synchronized with the horse's movement may command the rhythm of one or more devices or vibration modules placed on the rider's body. For example, a device or vibration module may be placed on the rider's back. In this configuration, the rider may learn to adapt their movement to the horse's movement by having their own motion stimulated in synchrony with the horse.

In some embodiments, information from at least one physiological sensor may trigger the start of the device. Non-limiting triggering events may include a change in average heart rate indicating stress, a change in regularity of the gait (change in tempo), or an appearance of a 0.9 Hz wave length that indicates a physiological or biomechanics problem such as pain, disease, etc. When the one or more sensors are mounted to the vibration module 70, the main controller board 10 may use those inputs to make a determination about the stress levels of the target individual. As the device detects signs of stress, the main controller board 10 may make slight adjustments to the vibration in an effort to reduce stress levels in the target individual.

Data from the sensors may be fed into the microprocessor to adjust the vibration. For example, data from accelerometers may be sent to the microprocessor to extract speed and rhythm info to identify the natural rhythm of the user. The interactive program may then adjust the rhythm of the vibration and phasing to the natural rhythm of the user, in order to match it and regularize it. This rhythm can be simultaneously manifested in a metronome placed in the device, giving an audible, sensorial marker synchronized with the vibration pattern. This may have an impact on the regularity of the heart rate and the breathing rhythm of the user.

In at least one example, a user with sever chronic back pain experienced reduced pain (from 10 on pain scale to 4-5) after using the device for 20 minutes, as needed. In some examples, the device may be applied once a day for 20 minutes. The user also experienced improved sleep, from waking 3-4 times per night to only waking 1 or no times per night. The user also noticed improvement in swallowing.

In at least one example, a user with severe cancer pain experienced reduced the pain after using the device with two vibration modules for 6 consecutive hours, followed by 3 times a day for 30 minutes for 4 days, followed by 1 time a day for 30 minutes. The vibration modules were placed on the user's chest and back.

In at least one example, a user with chronic pain due to use of chemotherapy, resulting in demyelination and polyneuropathy experienced reduced pain (from 10 to 5 average) after using the device daily for 20 minute sessions.

In at least one example, a user with lower back pain experienced reduced pain after using the device for several hours on their back at low power and high frequency. In another example, a user with chronic back pain experienced reduced pain after using the device with conductive fabric for about 45 minutes to 2 hours daily. In yet another example, a user with sciatic pain experienced reduced pain after using the device for 1 to 3 hours a day for about 30 days. In another example, a user with sciatic pain experienced reduced pain after using the device for 20 minutes at high frequency and high power.

In at least one example, a user with knee pain experienced relief after placing the device behind their knee once or twice daily for 20 minutes at high frequency and high power.

In at least one example, a user with chronic pain experienced reduced pain after using the device for 20 minutes at high frequency and high power once daily, or as needed.

In at least one example, a user with Parkinson's disease experienced a decrease in body spasms and improvement in stamina after using the device multiple times a day for 5 to 10 minutes on the user's neck, forearms, and thighs.

In at least one example, a user placed a device on their chest for 20 to 40 minutes at low power and low frequency before sleeping and experienced a reduction in snoring and insomnia. In another example, a user with insomnia experienced increased sleep after using the device on low frequency and low power for 20 minutes nightly.

In at least one example, a user with constipation experienced relief after using the device for 20 minutes.

In at least one example, a user with fibromyalgia experienced relief after using the device with two vibration modules (one at high frequency/low power and the other at low frequency/low power) for about an hour 2 to 3 times per week.

In at least one example, a user with migraines experienced relief after using the device for up to 5 minutes at a time on their face, back of head and neck, on neck, and behind the ears at high frequency and low power.

In an at least one example, a user with a contracted hand resulting from a stroke experienced relaxation and the ability to open their hand after using the device for 20 minutes several times a day at high frequency and high power.

In an at least one example, a user with amyotrophic lateral sclerosis experiences improved symptoms after using the device for 20 minutes several times a day at high frequency and high power.

In multiple examples, the device may be used to calm and/or train a horse. In one example, a rider used the device on their lower back for 15 minutes at high frequency and high power while riding the horse.

In at least one example, constipation in a horse was resolved after a device was placed on the belly of the horse for 20 minutes standing and 20 minutes lying down.

In at least one example, the device was used with young stallions, geldings and mares to keep them calm while introducing them to new things like clippers, main pulling, bags, water, etc. The device was attached to either the withers or upper neck area was applied for 20 to 40 minutes before introducing the object to them and maintaining the vibration.

In at least one example, a vibration module was placed on a horse at a spot 4 inches above the breast bone between the surcingle and the skin to stop a weaving habit (swinging head) in the horse. The device was used for about 20 minutes daily over a two-week period at high frequency and high power.

In at least one example, a device was placed under the cavesson noseband of 2 horses with a difficult mouth for about 45 minutes while riding the horse. In another example, a device was placed under the noseband of a horse with mouth issues.

In at least one example, a device was used on racehorses for 20 to 45 minute sessions at high frequency and high power for alleviating pain in the horse's feet, ankles, knees, and necks. In another example, a device was used on a horse with sore shins for 3 days with 60 minute sessions at high frequency and low power.

In at least one example, a device was used on a horse that was highly excitable and nervous. The horse was observed to relax after using the device for 45 minute sessions at high frequency and high power daily.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A therapy device, comprising:
a main controller board enclosed in a housing;
a power source operatively connected to the main controller board;
at least one vibration module operatively connected to the main controller board, the at least one vibration module comprising four or more motors, the at least one vibration module operable to generate a mechanical vibration; and
an input controller operatively connected to the main controller board, wherein the input controller is operable to control the at least one vibration module,
wherein the combination of the four or more motors in the at least one vibration module is configured to generate a multidirectional vibration in a user, and
wherein each of the motors is configured to drive through increasing and decreasing frequencies and not synchronized with the other motors, and to be paused at random periods of time not synchronized with the other motors, and
wherein the main controller board automatically selects a frequency of vibration for each motor in the at least one vibration module.

2. The device of claim 1, wherein the frequency of vibration of each motor is between about 0.0625 Hz and about 1500 Hz.

3. The device of claim 1, wherein the at least one vibration module comprises a first motor and a second motor of the four or more motors that vibrate perpendicular to one another.

4. The device of claim 3, wherein the at least one vibration module comprises a third motor of the four or more motors that vibrates in an oblique direction to the first and second motors.

5. The device of claim 1, wherein the input controller is an input device harness comprising at least two inputs.

6. The device of claim 1, further comprising a power switch harness operatively connected to the power source.

7. The device of claim 1, further comprising at least one sensor operatively connected to the at least one vibration module.

8. The device of claim 1, further comprising a magnet configured to be between the housing and the user.

9. The device of claim 1, further comprising a conductive fabric to secure the device to the user or to secure at least one electrical capacitor to the at least one vibration module.

10. The device of claim 1, comprising more than one vibration module, wherein each vibration module is configured to be placed on a separate area of a user's body from other vibration modules of the more than one vibration module.

11. The device of claim 10, wherein the vibration modules are configured to be placed bilaterally.

12. A method of using the device of claim 1, comprising:
placing at least one vibration module of the device of claim 1 at a location on a user;
engaging a power switch harness to turn the device on;
selecting a pulse width modulation for the at least one vibration module using the input controller; and disengaging the power switch harness after a period of time to turn the device off.

13. The method of claim 12, wherein the main controller board comprises at least one non-transitory computer readable medium storing instructions for a data collecting interactive program which when executed by at least one microprocessor, causes the at least one microprocessor to: receive input signals from the input controller, define a vibration frequency for each motor, and instruct the at least one vibration module to generate the multidirectional vibration.

14. The method of claim 13, further comprising receiving an input from a sensor to provide feedback to the main controller board to adjust the vibration.

15. The method of claim 13, wherein the device further comprises a magnet between the housing and the user.

16. A method of stimulating an autonomous or parasympathetic nervous system, the method comprising:
   placing the device of claim 1 on the skin of a user;
   selecting a power level for the at least one vibration module; and
   removing the at least one vibration module after a period of time,
   wherein the combination of the four or more motors in the at least one vibration module generates a multidirectional vibration in a user, and
   wherein each of the motors drives through increasing and decreasing frequencies not synchronized with the other motors and, and wherein each of the motors is paused at random periods of time not synchronized with the other motors.

17. The method of claim 16, wherein the at least one vibration module comprises a first motor and a second motor that vibrate perpendicular to one another.

18. The method of claim 17, wherein the at least one vibration module further comprises a third motor that vibrates in an oblique direction to the first motor and second motor.

19. The method of claim 16, wherein the at least one vibration module is placed on the skin of the user proximal to a vagus nerve.

20. The therapy device of claim 1, further comprising:
   at least one processor; and
   at least one non-transitory computer readable medium configured to store instructions for a data collecting interactive program which, when executed by the at least one processor, causes the at least one processor to: receive input signals, define a vibration, and instruct the at least one vibration module to generate a vibration.

21. The therapy device of 20, wherein the at least one non-transitory computer readable medium may cause a processor on a user's smartphone to execute the interactive program.

* * * * *